Matsushita et al.

[11] Patent Number: 4,530,794
[45] Date of Patent: Jul. 23, 1985

[54] IRON-TETRAPHENYLPORPHINE COMPLEX HAVING PHOSPHOCHOLINE GROUP

[75] Inventors: Yoh-ichi Matsushita; Etsuo Hasegawa; Kiyoshi Eshima, all of Tokushima; Eishun Tsuchida, Tokyo, all of Japan

[73] Assignee: Taiho Pharmaceutical Co., Ltd., Tokyo, Japan

[21] Appl. No.: 555,474

[22] Filed: Nov. 28, 1983

[30] Foreign Application Priority Data

Dec. 1, 1982 [JP] Japan .............................. 57-210840
Dec. 1, 1982 [JP] Japan .............................. 57-210841

[51] Int. Cl.³ ..................... C07D 487/22; C09B 47/00
[52] U.S. Cl. .................................. 260/245.91; 424/38
[58] Field of Search .................................. 260/245.91

[56] References Cited
U.S. PATENT DOCUMENTS 4,133,874   1/1979   Miller et al. .......................... 424/38
4,356,167  10/1982   Kelly .................................... 424/38

OTHER PUBLICATIONS

Hasegawa et al, "Liposomal Heme as Oxygen Carrier under Semiphysiological Condition", Biochem. and Biophys. Res. Communications, vol. 105, 1416–1419 (1982).
Chemistry Letters, No. 9, 1983, The Chemical Society of Japan, "Synthesis of Amphiphilic Porphinato Iron Complexes having Phosphorylcholine Groups", Yoh-ichi Matsushita et al, pp. 1387–1390.
Journal of the American Chemical Society, 97:6, pp. 1427–1439 (1975), Collman, et al.
Tetrahedron Letters, vol. 23, No. 10, pp. 1043–1046 (1982) Chandrakumar, et al.
Synthesis; pp. 517–518 (1975); Newkome, et al.

*Primary Examiner*—Richard L. Raymond
*Attorney, Agent, or Firm*—Frishauf, Holtz, Goodman & Woodward

[57] ABSTRACT

Disclosed is an iron-5,10,15,20-tetra($\alpha$, $\alpha$, $\alpha$, $\alpha$-o-substituted phenyl)porphine complex having one or four substituents with a phosphocholine group at the terminal end thereof. The substituents are positioned ortho of the phenyl group or groups.

5 Claims, 4 Drawing Figures

IRON-TETRAPHENYLPORPHINE COMPLEX HAVING PHOSPHOCHOLINE GROUP

BACKGROUND OF THE INVENTION

I. Field of the Invention

The present invention relates to an iron-tetraphenylporphine complex and, more particularly, to an iron-5,10,15,20-tetra($\alpha,\alpha,\alpha,\alpha$-o-substituted phenyl)porphine complex having phosphocholine groups. The present invention also relates to a process for preparing the complex and an agent capable of adsorbing and desorbing oxygen containing the complex.

II. Description of the Prior Art

Many attempts have been made to prepare oxygen-adsorbing and desorbing agents using synthetic iron(II)-porphine complexes. One successful example is iron(II)-5,10,15,20-tetra($\alpha,\alpha,\alpha,\alpha$-o-pivalamidophenyl)porphine complex reported by J. P. Collman et al., Journal of the American Chemical Society, 97, 1427 (1975). However, this complex can only function under limited conditions such as in anhydrous aprotic organic solvents or in a solid state, and it can not function under more general conditions such as in aqueous solvents. When industrial utilization such as oxygen enrichment, and utilizations in perfusion liquids for storing organs and as artificial blood used for living system as a useful oxygen-adsorbing and desorbing agent functioning under general conditions are considered, there is a strong demand for a material system which can adsorb and desorb oxygen effectively in water and, further, at room temperature or at a temperature of about 37° C.

E. Hasegawa et al. have taught in their paper, Biochemical and Biophysical Research Communications, 105, 1416 (1982), to enclose an iron(II)-5,10,15,20-tetra($\alpha,\alpha,\alpha,\alpha$-o-pivalamidophenyl)porphine complex in a liposome composed of a phospholipid. This complex is taken up in a hydrophobic region or liophilic layer of the liposome. It is reported that the complex, enclosed in a liposome, forms an oxygen complex stable at room temperature even if placed in water, and adsorbs and desorbs oxygen reversibly. Thus, to enclose a complex in a liposome is extremely effective in causing a complex to exhibit an adsobing and desorbing capability in water over a long period of time. It is to be noted, however, that the above-noted iron(II)-porphine complex is not easy to be solubilized in water because of its hydrophobic structure, and presents the difficulty that an amount of the complex to be embedded in a liposome of a given amount is small, resulting in that the adsorption and desorption capacity of the whole system is small.

SUMMARY OF THE INVENTION

It is, therefore, an object of the present invention to provide a novel iron-porphine complex which maintains an oxygen adsorption and desorption ability as high as that of an iron-5,10,15,20-tetra-($\alpha,\alpha,\alpha,\alpha$-o-pivalamidophenyl)porphine complex, and is easily dissolved in water or enclosed in a micelle comprising a variety of surface active agents or in a liposome comprising a phospholipid.

It is another object of the present invention to provide a process for preparing such a complex.

It is still another object of the present invention to provide an oxygen adsorbing and desorbing agent comprising such a complex as an active ingredient.

In order to achieve the above objects of the present invention, there is provided an iron-5,10,15,20-tetra($\alpha,\alpha,\alpha,\alpha$-o-substituted phenyl)porphine complex having a structure represented by the general formula:

where each R is identical and stands for (pivalamido group) or the group n is an integer from 1 to 20, and the central iron atom is divalent or trivalent.

The compound represented by general formula (I) according to the present invention is an amphiphilic compound in which the tetraphenylporphine ring and alkylene moiety or moieties comprise a hydrophobic part, and the phosphocholine moiety or moieties present at the terminal end or ends of the alkylene moiety or moieties comprises a hydrophilic part. As is well known in the art, surfactants which are capable of forming micelles and phospholipids which are capable of forming liposomes have both hydrophobic portions (mainly comprised of alkylene chains) and hydrophilic portions (comprised of, for example, polyethylene glycol group, tetraalkylammonium group, carboxylate group or phosphocholine group). The compound of formula (I) according to the present invention can be readily enclosed or embedded in the micelles and liposomes in an increased amount because of the structural similarity of the compound of the present invention to micelle-forming surfactants and liposome-forming phospholipids. Further, the porphyrine moiety of the compound of the present invention which exhibits oxygen adsorbing and desorbing functions is embedded deep in the hydrophobic regions (lipid regions) of the micelles and liposomes because of its hydrophobic nature and thus placed in an environment excluding water, resulting in that oxygen adsorbing and desorbing capability of the compound of the present invention and the stability of its oxygenated complex are equal to or superior to those of the prior art compound.

Thus, the compound of the present invention, if enclosed in liposomes of phospholipid, is expected to provide an oxygen adsorbing and desorbing system which can carry oxygen in an increased amount because the compound of the invention can be enclosed in an increased amount in liposomes formed of a given amount of phospholipids.

DETAILED DESCRIPTION OF THE PREFERRED EMBODIMENTS

The compounds of general formula (I) according to the present invention will be described in more detail along with the process for preparing them.

As is apparent from the definition of general formula (I), the present invention provides complexes of two types represented by formulas (II) and (III) as follows:

(II)

(III)

(1) Preparation of Complexes of Formula (I):
(i) Complexes of Formula (II) in which All of Symbols R in Formula (I) are Groups Each Represented by Formula:

According to the present invention, such a complex can be prepared by the following procedures. An ω- benzyloxy-2,2-dimethylalkanoic acid chloride represented by formula (A):

(A)

where n is an integer from 1 to 20, is first reacted with 5,10,15,20-tetra(α,α,α,α-o-aminophenyl)porphine reported by J. P. Column et al. in Journal of the American Chemical Society, 97, 1427 (1975) (to be referred to as H₂TamPP hereinafter) represented by formula (B):

(B)

in the presence of a base, to provide a benzyl ether compound represented by formula (C):

(C)

wherein n has the same meaning as given above.

The benzyl ether compound of formula (C) is then reacted with anhydrous aluminum trichloride in the presence of anisole to remove the four benzyl groups, whereby an alcoholic compound represented by formula (D) below is obtained:

(D)

wherein n has the same meaning as given above.

The alcoholic compound of formula (D) is then reacted with a ferrous halide in the presence of pyridine to provide a compound represented by formula (E):

(E)

wherein X is a halogen atom and n has the same meaning as given above.

The compound of formula (E) is then reacted with 2-chloro-2-oxo-1,3,2-dioxaphospholane to provide a phosphate ester derivative which in turn is reacted with an excessive amount of trimethylamine to cause phosphocholination. Thus, the compound in which each symbol R in general formula (I) has phosphocholine group is obtained (formula (II)).

The reaction of the carboxylic acid chloride of formula (A) with H₂TamPP is effected using the former in an amount of, for example, 4 moles or more, preferably 6 to 16 moles per mole of the latter in an anhydrous aprotic solvent capable of dissolving H₂TamPP, preferably such as tetrahydrofuran, dichloromethane, chloroform, N,N-dimethylformamide or acetone. This reaction is carried out at temperatures ranging from 0° C. to about 30° C. for about 3 hours to about 24 hours in the presence of a base preferably such as pyridine, triethylamine or 4-(N,N-dimethylamino)pyridine in an amount of, for example, 4 moles or more, preferably 6 to 16 moles per mole of H₂TamPP. After the reaction is completed, the reaction mixture is poured into water, extracted with chloroform, and evaporated to distill off the solvent from the extract. The residue is purified by means of silica gel column chromatography to give the benzyl ether compound of formula (C). Purification may be carried out by recrystallization from an appropriate solvent such as methanol, ethanol and a mixture thereof with benzene, as needed.

In order to remove the four benzyl groups from the benzyl ether compound of formula (C), the benzyl ether compound is reacted with anhydrous aluminum chloride in an amount of 4 moles or more, preferably 4 to 100 moles per mole of the benzyl ether compound in a mixed solvent of dichloromethane and nitromethane in the presence of anisole in an amount of 4 to 100 moles per mole of the benzyl ether compound at −5° C. to 30° C., and preferably from 15° C. to 25° C. for 2 hours to 12 hours. The reaction mixture is then poured into iced water and extracted with chloroform. The extract is washed with water and then with a 4% sodium hydrogen carbonate aqueous solution. The chloroform layer is separated and dried over salt cake. After the chloroform is evaporated, the residue is recrystallized from benzene or a dichloromethane-benzene mixture to provide the alcoholic compound of formula (D).

The introduction of an iron atom into the compound of formula (D) is carried out by reaction with ferrous bromide in an amount ranging from 1 to 100 moles per mole of the alcoholic compound in the presence of pyridine in an amount ranging from 1 to 100 moles per mole of the alcoholic compound, in anhydrous tetrahydrofuran refluxed under a nitrogen gas atmosphere, according to the procedures described by J. P. Collman et al., Journal of the American Chemical Society, 97, 1427 (1975). The reaction mixture is concentrated under reduced pressure, and the residue is purified by means of alumina or silica gel column chromatography using chloroform or a mixed solvent of chloroform and methanol. The product is then treated with hydrobromic acid in an amount of 1 mole or more per mole of the iron-porphyrine at 0° C. to 30° C. The thus obtained compound of formula (E) has the central iron atom in the trivalent state and one bromine ion as a counter ion. In this case, the use of hydrochloric acid in place of hydrobromic acid gives a chlorine ion as a counter ion, and the use of hydroiodic acid provides an iodine ion.

The phosphocholination of the compound of formula (E) can be carried out by procedures which are improved from those of the phosphocholination reaction of a hydroxyl group as reported by N. S. Chandrakumar et al., Tetrahedron Letters, 23, 1043 (1982). Specifically, 2-chloro-2-oxo-1,3,2-dioxaphospholane in an amount of 1 to 2 mole equivalents for one hydroxyl group in the compound of formula (E) is added dropwise at 0° C. to room temperature to the compound of formula (E) in the presence of triethylamine in an amount of 1 to 2 mole equivalents for one hydroxyl group in the compound of formula (E) in an anhydrous aprotic solvent such as dichloromethane, chloroform or benzene. The mixture is then reacted at room temperature for from 6 to 24 hours. The solvent is distilled off under reduced pressure to leave a residue which in turn is dissolved in acetonitrile or N,N-dimethylformamide. After the addition thereto of trimethylamine in an amount ranging from 1 to 100 mole equivalents for one hydroxyl group in the compound of formula (E), the mixture is sealed in a stainless steel container and then reacted at 50° C. to 65° C. for 12 to 24 hours. The reaction mixture is filtered to leave a brown precipitated material which in turn is washed with acetone and purified by means of column chromatography using an appropriate gel such as Sephadex G-25, Sephadex LH-60 (each available from Pharmacia Fine Chemicals) or Toyopearl HW-40 (Toyo Soda K.K) with methanol or water used as a solvent to provide a desired, novel[iron-5,10,15,20-tetra(α,α,α,α-o-substituted phenyl)porphine]complex having four phosphocholine groups as represented by formula (II).

(ii) Complexes of Formula (III) in which all of symbols R in formula (I) are each pivalamido group:

According to the present invention, the complex can be prepared in the following manner. An equimolar amount of the carboxylic acid chloride of formula (A) is first reacted with an equimolar amount of T₂TamPP, and the reaction mixture is then reacted with 3 moles equivalent or more of pivaloyl chloride to provide a compound represented by formula (F):

wherein n has the same meaning as given above, which in turn is reacted with anhydrous aluminum chloride in the presence of anisole to remove the benzyl group, whereby the compound of formula (G) is obtained:

wherein n has the same meaning as given above.

The compound of formula (G) is then reacted with ferrous bromide in the presence of pyridine to introduce an iron atom therein, thereby providing the compound of formula (H):

wherein n has the same meaning as given above.

The compound of formula (H) is reacted with 2-chloro-2-oxo-1,3,2-dioxaphospholane and then with an excessive amount of trimethylamine to provide the complex according to the present invention in which all the symbols R in general formula (I) are each pivalamido group. The central iron atom of this complex is usually trivalent.

In preparing the complex of formula (III), the reaction of the acid chloride of formula (A) with $H_2TamPP$ can be carried out under the same conditions under which the carboxylic acid chloride of formula (A) is reacted with $H_2TamPP$ of formula (B) in the preparation of the complex of formula (II) with the exception that the carboxylic acid chloride of formula (A) and $H_2TamPP$ of formula (B) are used in each one equimolar equivalent. After the completion of this reaction, 3 molar equivalents or more, and preferably from 3 to 10 molar equivalents, of pivaloyl chloride is added to the reaction mixture, and the mixture is further reacted at room temperature for about 1 to about 24 hours. After the reaction is completed, the reaction mixture is poured into water and then extracted with ether, chloroform or dichloromethane. The extract is washed with water and the organic layer is dried over salt cake, which in turn is concentrated. The residue is then purified by silica gel chromatography to provide the compound of formula (F).

In order to remove the benzyl group from the compound of formula (F), the reaction is carried out in the same manner as the reaction for the removal of the benzyl group from the compound of formula (C), with the exception that anisole is used in an amount ranging from 1 mole to 100 moles per mole of the compound of formula (F) and anhydrous aluminum chloride is used in an amount ranging from 1 mole to 50 moles per mole of the compound of formula (F). Thus, the compound of formula (G) is obtained.

The introduction of an iron atom into the compound of formula (G) may be carried out in the same manner as in the process for introducing an iron atom into the compound of formula (D).

The phosphocholination of the compound of formula (G) may be effected in accordance with the phosphocholination of the compound of formula (E).

The carboxylic acid chloride of formula (A) to be employed as a starting material for the complexes of general formulas (II) and (III) is believed to be novel, and may be prepared in the following manner. An ω-benzyloxyalkyl halide of formula:

wherein n has the same meaning as given above, and X' is chlorine or bromine is reacted with lithium dianion of 2-methylpropionic acid prepared according to the method reported by George R. Newkome et al. in Synthesis, 1975, 517, in a molar ratio of the former to the latter ranging from 1:1 to 1:3. The reaction is carried out first at temperatures as low as −70° C. to −20° C. for 1 hour to 5 hours and then at temperatures as high as 30° C. to 45° C. for 3 hours to 48 hours. The reaction mixture is subjected to decomposition with cold dilute hydrochloric acid, and is then extracted with a solvent such as diethyl ether, chloroform and dichloromethane to provide a crude product which in turn is recrystallized, for example, from petroleum ether, n-hexane or n-heptane, to yield an ω-benzyloxy-2,2-dimethylalkanoic acid as colorless crystal. This product is further reacted with thionyl chloride in an amount ranging from 1 to 3 moles per mole of the alkanoic acid at a temperature from 20° C. to 50° C. for 3 hours to 24 hours in an aprotic solvent, preferably benzene or carbon tetrachloride. The reaction may be effected without the use of the solvent. The reaction mixture is concentrated under reduced pressure to yield an ω-benzyloxy-2,2-dimethylalkanoic acid chloride as represented by formula (A).

The halide of formula (J) wherein n is 1 and X' is chlorine may be synthesized according to the method described by A. J. Hill et al., Journal of the American Chemical Society, 48, 257 (1926). The halide of formula (J) wherein n is 2 and X' is bromine may be synthesized according to the method described by P. Cresson in Bulletin de la Société Chemique de France, 1964, 2629. Further, the halide of formula (J) wherein n is an integer from 3 to 20 and X' is bromine may be prepared by the reaction of a corresponding $\alpha,107$-dibromoalkane with an equimolar amount of sodium benzyloxide under reflux in benzene.

(2) Oxygen Adsorbing and Desorbing Functions of Complex of Formula (I):

The complex according to the present invention as obtained by the procedures described hereinabove has the central iron atom in a trivalent state. In order to provide the iron(III)-porphine complex with adsorbing and desorbing functions, it is necessary to have the central iron atom reduced to a divalent state and at the same time coordinated with an appropriate basic ligand as an axial ligand. The basic ligand occupies one or two of the two axial coordination sites of the central iron atom located in the direction orthogonal to the plane including the porphine ring.

(i) Basic Ligand to be Used:

The ligand to be used according to the present invention is a basic compound containing an atom having a lone electron pair, particularly nitrogen atom. Preferred examples of such ligands include an imidazole compound represented by the general formula (K):

wherein $R_1$, $R_2$ and $R_3$ are independently each hydrogen, methyl group or ethyl group; and $R_4$ is hydrogen, a $C_1$-$C_{20}$ alkyl group, phenyl group, benzyl group, phenethyl group or trityl group.

Examples of the imidazole compound of formula (K) are imidazole, 1-methylimidazole, 2-methylimidazole, 3,4-dimethylimidazole, 1-ethylimidazole, 1,2-dimethylimidazole, 1-phenethylimidazole, 1-phenethyl-2-methylimidazole, 1-laurylimidazole, 1-lauryl-2-methylimidazole, 1-tritylimidazole, 1-trityl-2-methylimidazole, 1-cyclohexylimidazole, 1-cyclohexyl-2-methylimidazole, 1-stearylimidazole, and 1-phenylimidazole.

As is well known, the coordination of an iron-porphine complex with a basic ligand is performed under an equilibrium reaction so that it is preferred to make the basic ligand present in an amount in excess of the iron-porphine complex. In the present invention, the basic ligand may be used in an amount ranging from 1 mole to 1,000 moles, and preferably from 5 moles to 200 moles per mole of the complex of formula (I).

The complex of formula (I) may be subjected to coordination with the basic ligand by simply being mixed with the basic ligand in an aqueous medium such as water, physiological saline solution, Krebs-Ringer solution or a phosphate buffer solution. In instances where a basic ligand which is insoluble or sparingly soluble in water is employed, a treatment for making the basic ligand soluble in water is required.

The substituted imidazole of formula (K), for example, in which $R_4$ is a $C_5$-$C_{20}$ alkyl group, phenyl, benzyl, phenethyl or trityl group, is sparingly soluble in water. This substituted imidazole is first dissolved in a small amount of an organic solvent such as ether, acetone, chloroform or methanol, and the solution is mixed with an $\alpha$- or $\beta$-cyclodextrin aqueous solution, in an amount of 1 to 2 mole of imidazole per mole of dextrin, followed by stirring at room temperature for 1 to 5 hours. The mixture is then lyophilized to give a white or pale yellow powder which in turn is washed with anhydrous ether and dried in vacuo at 30° C. to 60° C. to provide the substituted imidazole included in the cyclodextrin. This clathrate compound is soluble in water and is found to have cyclodextrin and imidazole in a molar ratio of 1 to 1 as a result of calibration of the integral curve obtained by the proton nuclear magnetic resonance spectra.

It is also possible to make the water-insoluble or sparingly soluble imidazole water-soluble by using a synthetic surfactant including a non-ionic surfactant such as Triton X-100 (Rohm and Haas), a cationic surfactant such as cetyl trimethyl ammonium bromide, or a water-soluble polymer such as polyvinyl pyrrolidone, polyethylene glycol, Pluronic F68 (Wyandotte Chemical), dextran, albumin, poly-L-glutamic acid or the like. Where a surfactant is employed, the imidazole compound is taken up into its micelles.

More preferably, a naturally occurring or synthetic phospholipid such as egg yolk lecithin, soybean lecithin, dipalmitoyl phosphatidyl choline, dimyristoyl phosphatidyl choline, distearoyl phosphatidyl choline, phosphatidyl ethanolamine, phospatidyl inositol, sphingomyelin, phosphatidic acid or a mixture thereof is mixed with the substituted imidazole compound sparingly soluble in water in an amount ranging from 5 to 200 moles equivalents, and preferably from 10 to 150 moles per mole of the substituted imidazole compound, and the mixture is ultrasonicated in the aqueous medium to provide a substituted imidazole dispersed aqueous solution in which the imidazole compound is embedded in liposomes of phospholipids.

It is of course to be understood that a water-soluble substituted imidazole can be used as it is without treatment for making it soluble in water.

(ii) Reduction of Centrol Iron Atom:

The reduction of the central iron atom of the complex of formula (I) having a trivalent iron atom as the central atom to the divalent state may be carried out by reducing the complex with a reducing agent such as solium dithionite, sodium borohydride or ascorbic acid in an amount ranging from an equimolar equivalent to a slightly excessive amount, for example, from 2-fold equivalent to 20-fold equivalent with respect to the complex. The reduction reaction is conducted at a temperature from 0° C. to 50° C. for a period of time from 0.1 hour to 1 hour.

The reduction may also be effected using hydrogen gas. For example, the iron (III) complex of formula (I) is dissolved with palladium black or palladium carbon in an amount ranging from 0.5 to 10 parts by weight per part of the complex in an appropriate solvent such as methanol and ethanol, and hydrogen gas is blown into the solution. This reaction is carried out at a temperature from 0° C. to 30° C. for a period of time from 0.1 hour to 1 hour. The hydrogen gas is used at a rate of 20 to 200 ml/min. After the completion of the reduction, the reaction mixture is filtered to remove the catalyst used, and the solvent is distilled off under reduced pressure.

The reduction may further be effected using an enzymatic reducing agent by the procedures as reported by E. Hasegawa et al. in Biochemical and Biophysical Research Communications, 104, 793 (1982).

In each of the reduction methods, it is preferred to effect the reduction in the presence of the basic ligand as set forth hereinabove. This allows both the reduction of the central iron atom to the divalent state and, at the same time, the coordination of the basic ligand with the reduced central iron atom, thereby creating functions of absorption and desorption of oxygen.

The complex of formula (I) according to the present invention in which the central iron (II) atom is coordinated with the ligand can be included in micelles formed by the synthetic surfactant as enumerated hereinabove or in liposomes formed by the phospholipid as enumerated hereinabove, thereby allowing the life of the oxygenated complex provided by the adsorption of oxygen to be extended. This clathrate inclusion of the complex into the micelles or liposomes may be carried out utilizing the techniques involving the water-solubilization of the imidazole compound sparingly soluble in water. It is to be understood, however, that the imidazole compound to be used is not limited to one that is sparingly soluble in water.

A well known infusion ingredient such as dextran, hydroxyethyl starch, poly-L-glutamic acid, various saccharides, amino acids, electrolytes or the like may be added to the aqueous medium in which the complex according to the present invention is dispersed, at a rate ranging from 1 to 30% (w/v). In forming the liposomes, cholesterol may be used as one of the components of liposomes, in an amount up to 30 mole%.

The oxygen adsorbing and desorbing agent comprising the complex of formula (I) in which the central iron atom is divalent and is coordinated with the basic ligand as enumerated hereinabove is expected to be of value in industrial utilization such as for oxygen enrichment and as a perfusion solution preservative for organs and applicable to living systems.

The present invention will be described in more detail by way of working examples.

EXAMPLE 1 (Formula (C), n=10)

5,10,15,20-Tetra($\alpha,\alpha,\alpha,\alpha$-o-aminophenyl)porphine (hereinafter referred to as H$_2$TamPP) was synthesized according to the procedures described in J. P. Collman et al., Journal of the American Chemical Society, 97, 1427 (1975).

Pyridine, 0.81 ml, was added to a solution of 1.0 g of H$_2$TamPP in 40 ml of anhydrous tetrahydrofuran, and 3.53 g of 12-benzyloxy-2,2-dimethyldodecanoyl chloride was then added dropwise to the mixture. After the mixture was reacted at room temperature for 3 hours, it was extracted with ether and then washed with water. The separated ether layer was dried over salt cake and then concentrated under reduced pressure to yield a crude product. The crude product was purified by means of silica gel column chromatography with a benzene: ether (volume ratio, 15:1) mixed solvent to give 1.69 g (yield 60%) of 5,10,15,20-tetra[$\alpha,\alpha,\alpha,\alpha$-o-(12-benzyloxy-2,2-dimethyldodecanamido)phenyl]porphine as a brown oily material.

Infrared absorption spectra (CHCl$_3$): $\nu$: 3440, 3330, 3000, 2930, 2860, 1680, 1580, 1510, 1450, 1300, 1100, 970, 910, 700 cm$^{-1}$.

Proton NMR spectra (CDCl$_3$) $\delta_{ppm}$: −2.6 (2H, s, >NH in the porphine ring), −0.23 (24H, s, —C(CH$_3$)$_2$CONH—), 3.46 (8H, t, PhCH$_2$OCH$_2$CH$_2$—), 4.50 (8H, s, PhCH$_2$O—), 7.32 (20H, s), 8.82 (8H, s).

EXAMPLE 2 (Formula (D), n=10)

Anisole, 2 ml, was added to a solution of 1.68 g of 5,10,15,20-tetra[$\alpha,\alpha,\alpha,\alpha$-o-(12-benzyloxy-2,2-dimethyldodecanamido)phenyl]porphine in a mixed solvent of 25 ml of anhydrous dichloromethane and 25 ml of nitromethane. Anhydrous aluminum trichloride, 2 g, was further added to this mixture, and the mixture was then reacted at a room temperature for 4 hours. The reaction mixture was poured into 100 ml of iced water to decompose excess aluminum trichloride, and it was then extracted with dichloromethane. The separated dichloromethane layer was washed with water and then with a 10% sodium hydrogen carbonate aqueous solution and separated. The layer was then dried over salt cake and concentrated under reduced pressure. The residue was recrystallized from benzene to give 5,10,15,20-tetra-[$\alpha,\alpha,\alpha,\alpha$-o-12-hydroxy-2,2-dimethyldodecanamido)phenyl]porphine as violet plate cryatal with a yield of 1.10 g (80%). M.P. 127° to 129.5° C.

Field desorption mass spectrum: 1579 (M+1)$^+$.

Infrared absorption spectra (KBr): $\nu$: 3600–3350 (broad), 3440, 3330, 2940, 2860, 1690, 1585, 1515, 1450, 1302, 1060, 970, 810, 770, 740 cm$^{-1}$.

Proton NMR spectra (CDCl$_3$): $\delta_{ppm}$: −2.59 (2H, s, pyrrole >NH), −0.22 (24H, s, —C(CH$_3$)$_2$—CONH—), 3.64 (8H, t, HOCH$_2$CH$_2$—), 7.15 (4H, s), 7.36 −8.73 (16H, m), 8.82 (8H, s). It is to be noted that the absorption peaks at 4.50 (8H, s) originating from the benzyl group and at 7.32 (20H, s) disappeared.

Elemental analysis: C$_{100}$H$_{138}$N$_8$O$_8$; Calculated (%): C: 76.00, H: 8.80, N: 7.09 ; Found (%): C: 75.62, H: 8.90, N: 7.09.

EXAMPLE 3 (Formula (E), N=10)

Pyridine, 0.3 ml, was added to a solution of 0.65 g of 5,10,15,20-tetra[$\alpha,\alpha,\alpha,\alpha$-o-(12-hydroxy-2,2-dimethyldodecanamido)phenyl]porphine in 50 ml of anhydrous tetrahydrofuran, and the mixture was purged with nitrogen gas. Ferrous bromide tetrahydrate, 2.0 g, was added to this mixture, and the mixture was refluxed under nitrogen for 3 hours. The reaction mixture was extracted with chloroform and then washed with water. The separated chloroform layer was dried over salt cake and the solvent was distilled off under reduced pressure. The resultant residue was subjected to alumina column chromatography with a mixed solvent of chloroform/methanol (volume ratio, 9/1). The eluate was stirred with 2 ml of 48% hydrobromic acid and then dried over salt cake. It was then evaporated to dryness to yield bromo{5,10,15,20-tetra[$\alpha,\alpha,\alpha,\alpha$-o-(12-hydroxy-2,2-dimethyldodecanamido)phenyl]porphinato}iron (III) as a black violet solid with a yield of 0.38 g (54%). M.P. 76° to 79° C.

Field desorption mass spectrum: 1713 (M+1)$^+$. It is to be noted that this spectrum was meausued to be the molecular weight 1712 of C$_{100}$H$_{136}$N$_8$O$_8$FeBr.

Infrared absorption spectra (KBr): ν: 3600-3150 (broad), 3440, 2930, 2860, 1690, 1580, 1510, 1440, 1300, 1075, 1000, 805, 760, 715 cm$^{-1}$.

Elemental analysis: $C_{100}H_{156}N_8O_8FeBr$; Calculated (%): C: 70.13, H: 8.00, N: 6.54; Found (%): C: 70.37, H: 8.40, N: 6.63.

EXAMPLE 4 (Formula (II), n=10)

The phosphocholination of the tetraalcohol derivative obtained in Example 3 was effected according to the method reported in N. S. Chandrakumar et al., Tetrahedron Letters, 23, 1043 (1982). Specifically, 0.07 ml of triethylamine and 0.08 g of 2-chloro-2-oxo-1,3,2-dioxaphospholane were added to a solution of 0.15 g of bromo{5,10,15,20-tetra[α,α,α,α-o-(12-hydroxy-2,2-dimethyldodecanamido)phenyl]porphinato}iron (III) in 10 ml of anhydrous dichloromethane, and the mixture was reacted at room temperature for 12 hours. The completion of the reaction was confirmed by observing the disappearance of a spot at an Rf value of 0.30 and the formation of a spot at an Rf value of 0.40 by means of silica gel thin layer chromatography (solvent:-chloroform/methanol=10/1). The solvent was distilled off under reduced pressure and the resultant residue was dissolved in 25 ml of anhydrous acetonitrile. Trimethylamine 5 ml, was added to this solution at −60° to −40° C., and the mixture was sealed in a stainless pressure vessel. The mixture was then heated to 60° to 65° C. and reacted for 16 hours. After cooling to room temperature, the mixture was filtered to give a black precipitate which in turn was dissolved in methanol and purified through a gel column packed with "Sephadex LH-60". The eluate was evaporated to dryness and dried in vacuo over phosphorus pentoxide to give, as a black solid, iron (III)-5,10,15,20-tetra{α,α,α,α-o-[12-(2'-trimethylammonioethoxy)phosphinatoxy-2,2-dimethyl-dodecanamido]phenyl}porphine complex with a yield of 0.18 g (90%). M.P. 145° to 150° C.

Infrared absorption spectra (KBr): ν: 3650-3150 (broad), 3430, 2940, 2860, 1690, 1580, 1510, 1440, 1220, 1080, 1000, 950, 800, 760, 710 cm$^{-1}$.

Visible absorption spectra (H$_2$O): λ$_{max}$: 412, 564 nm.

$^{13}$C—NMR spectra data
Compound —R $^{13}$C—NMR spectra data
Compound —R

| Carbon | δ$_{TMS}$ (ppm) | | |
|---|---|---|---|
| | (C) (n = 10) | (D) (n = 10) | (II) (n = 10) |
| 1 | 174.7 | 174.9 | 176.6 |
| 2 | 42.5 | 42.3 | 45.4 |
| 3 | 41.1 | 41.0 | 43.6 |
| 4 | 24.9 | 24.9 | 27.6 |
| 5 | 30.0 | 29.9 | 30.5 |
| 6 | 29.5 | 29.3 | 29.5 |
| | 29.7 | 29.9 | 30.5 |
| 7 | 26.2 | 25.7 | 27.6 |
| 8 | 29.7 | 32.7 | 31.7 |
| 9 | 70.4 | 62.8 | 66.6 |
| 2-Me | 24.1 | 24.1 | 26.6 |
| a | 72.7 | | 60.2 |
| b | 138.6 | | 66.8 |
| c | 128.2 | | 54.7 |
| d | 127.5 | | |
| e | 127.8 | | |

Solvent: (C), (D) in CDCl$_3$ and (II) in CD$_3$OD + NaCN/D$_2$O.

EXAMPLE 5 (Formula (C), n=18)

1,18-Dibromooctadecane was synthesized, for example, by the procedures reported in Lester Friedman and Arnon Shani, Journal of the American Chemical Society, 96, 7101-7103 (1974). Specifically, in a manner similar to the procedures used in Example 17, 18-benzyloxyoctadecanyl bromide was produced at a yield of 18.3 g (41%) from 42 g of 1,18-dibromooctadecane used in place of 1,10-dibromodecane. This product, 18 g, was reacted with an equimolar amount of lithium dianion of 2-methylpropionic acid, and the reaction mixture was extracted in the same manner as in Example 17 to give a crude oily material which in turn was purified by means of silica gel column chromatography using a mixed solvent of benzene/ether (volume ratio 15/1). The resultant product was 20-benzyloxy-2,2-dimethyleicosanoic acid as a colorless crystalline material, and the yield thereof was 5.7 g (31%). M.P. 72° to 73° C.

Elemental analysis: $C_{29}H_{50}O_3$; Calculated (%): C: 77.97, H: 11.28; Found (%): C: 78.25, H: 11.21.

Infrared absorption spectra (KBr): ν: 2930, 2860, 1705, 1470, 1130, 1120, 950, 740, 700 cm$^{-1}$.

Proton NMR spectra (CDCl$_3$): δ$_{ppm}$: 1.18 (6H, s, —C(CH$_3$)$_2$COOH), 1.25 (32H, brs, PhCH$_2$OCH$_2$(CH$_2$)$_{16}$CH$_2$—), 3.46 (2H, t, J=6.5 Hz, PhCH$_2$OCH$_2$CH$_2$—), 4.50 (2H, s, PhCH$_2$O—), 7.33 (5H, m, proton of the benzene ring).

The resultant carboxylic acid, 5.2 g, was reacted with 4 ml of thionyl chloride at room temperature for 4 hours and then concentrated under reduced pressure to give 20-benzyloxy-2,2-dimethyleicosanoyl chloride as a colorless solid with a yield of 5.6 g.

Infrared absorption spectra (CCl₄): ν: 2930, 2860, 1790, 1460, 1365, 1100, 905, 700 cm⁻¹.

A mixture of 5.6 g of the resultant 20-benzyloxy-2,2-dimethyleicosanoyl chloride and a solution of 1.3 g of H₂TamPP in 50 ml of anhydrous tetrahydrofuran and 1.5 ml of pyridine was reacted under the same conditions as in Example 1, and was post-treated and purified to give 3.70 g (yield 80%) of 5,10,15,20-tetra[α,α,α,α-o-(20-benzyloxy-2,2-dimethyleicosanamido)phenyl]porphine. M.P. 33° to 35° C.

Elemental analysis: $C_{160}H_{230}N_8O_8$; Calculated (%): C: 80.29, H: 9.68, N: 4.68; Found (%): C: 80.11, H: 9.88, N, 4.77.

Infrared absorption spectra (KBr): ν: 3440, 2920, 2850, 1690, 1580, 1510, 1450, 1360, 1300, 1100, 965, 800, 750 cm⁻¹.

Proton NMR spectra (CDCl₃): δ$_{ppm}$: −2.60 (2H, s, >N—H in the porphine ring), −0.22 (24H, s, —C(CH₃)₂—CONH—), 3.45 (8H, t, J=6.4 Hz, PhCH₂OCH₂CH₂—), 4.49 (8H, s, PhCH₂O—),

8.82 (8H, s, proton at the beta position of the porphine ring).

EXAMPLE 6 (Formula (D), n=18)

5,10,15,20-tetra[α,α,α,α-o-(20-benzyloxy-2,2-dimethyleicosanamido)phenyl]porphine, 0.5 g, was reacted with 6 g of anhydrous aluminum trichloride in a mixed solvent of 30 ml of dichloromethane and 15 ml of nitromethane in the presence of 3 ml of anisole, in the same manner as in Example 2. The reaction mixture was likewise post-treated, extracted and evaporated to dryness under reduced pressure. The resultant residue was purified through silica gel column chromatography with a chloroform/methanol (15/1) solvent mixture, and recrystallized from a solvent mixture of dichloromethane and methanol to give 1.89 g (yield 64%) of 5,10,15,20-tetra[α,α,α,α-o-(20-hydroxy-2,2-dimethyleicosanamido)phenyl]porphine as red brown acicular crystal.

Infrared absorption spectra (KBr): ν: 3430, 3320, 2920, 2860, 1675, 1580, 1510, 1470, 1450, 1300, 970, 805, 760, 720 cm⁻¹.

Proton NMR spectra (CDCl₃): δ$_{ppm}$: −2.60 (2H, s, >N—H in the porphine ring), −0.21 (24H, s, —C(CH₃)₂—CONH—), 3.69 (8H, t, J=64 Hz, HOCH₂CH₂—), 7.14 (4H, s, amido—CONH—), 8.82 (8H, s, proton at the beta position of the porphine ring).

Elemental analysis: $C_{132}H_{202}N_8O_8$; Calculated (%): C: 78.14, H: 9.98, N: 5.52; Found (%): C: 78.42, H: 10.20, N: 5.39.

EXAMPLE 7 (Formula (E), n=18)

5,10,15,20-tetra-[α,α,α,α-o-(20-hydroxy-2,2-dimethyleicosanamido)phenyl]porphine, 1.06 g, was reacted and post-treated in the same manner as in Example 3, and was then purified by means of silica gel column chromatography with a mixed solvent of chloroform/methanol (25/1). The resultant product was recrystallized from a dichloromethane/methanol mixture to give 0.82 g (yield 73%) of bromo{5,10,15,20-tetra[α,α,α,α-o-(20-hydroxy-2,2-dimethyleisosanamido)phenyl]porphinato}iron(III) as black violet crystal. M.P. 49° to 50° C.

Infrared absorption spectra (KBr): ν: 3430, 2930, 2860, 1690, 1580, 1510, 1460, 1440, 1300, 1000, 800, 760, 720 cm⁻¹.

Elemental analysis: $C_{132}H_{200}N_8O_8FeBr$ (1/2)CH₂Cl₂; Calculated (%): C: 72.16, H: 9.19, N: 5.08; Found (%): C: 72.41, H: 9.09, N: 4.92.

EXAMPLE 8 (Formula (II), n=18)

bromo{5,10,15,20-tetra[α,α,α,α-o-(20-hydroxy-2,2-dimethyleicosanamido)phenyl]porphinato}iron(III), 0.55 g, was reacted with 0.30 g of 2-chloro-2-oxo-1,3,2-dioxaphospholane in the presence of 0.3 ml of triethylamine in the same manner as in Example 4, and the reaction mixture was concentrated under reduced pressure. The resultant residue was then dissolved in a mixed solvent of 15 ml of N,N-dimethylformamide and 15 ml of acetonitrile, and the solution was reacted after the addition of 10 ml of trimethylamine. The reaction mixture was post-treated and purified in the same manner as in Example 4 to give 0.45 g (yield 61%) of iron-(III)-5,10,15,20-tetra{α,α,α,α-o-[20-(2'-trimethylammonioethoxy)phosphinatoxy-2,2-dimethyleicosanamido]phenyl}porphine complex as a black solid. M.P. 235° to 237° C.

Infrared absorption spectra (KBr): ν: 3430 (broad), 2940, 2860, 1690, 1590, 1515, 1470, 1440, 1300, 1230, 1090, 1000, 970, 810, 760, 730 cm⁻¹.

Elemental analysis: $C_{152}H_{248}N_{12}O_{20}P_4Fe$·9H₂O; Calculated (%): C: 62.83, H: 9.23, N: 5.78; Found (%): C: 62.55, H: 9.42, N: 5.99.

EXAMPLE 9

Benzyloxymethyl chloride was synthesized according to the procedures described in A. J. Hill et al., Journal of the American Chemical Society, 48, 257 (1926), and 10.96 g of the product was reacted with an equimolar amount of lithium dianion of 2-methylpropionic acid. The product was recrystallized from n-hexane to give 7.75 g (yield 53%) of 3-benzyloxy-2,2-dimethylpropionic acid. M.P. 72° to 74° C.

Infrared absorption spectra (KBr): ν: 3400–2400 (broad), 1700, 1480, 1320, 1250, 1120, 940, 740, 700 cm$^{-1}$.

Proton NMR spectra (CDCl$_3$): $\delta_{ppm}$: 1.23 (6H, s, —CH$_2$C(CH$_3$)$_2$COOH), 3.47 (2H, s, PhCH$_2$OCH$_2$C(CH$_3$)$_2$—), 4.55 (2H, s, PhCH$_2$O—), 7.31 (5H, s, proton of the phenyl ring).

Elemental analysis: C$_{12}$H$_{16}$O$_3$; Calculated (%): C: 69.20, H: 7.75; Found (%): C: 69.43, H: 7.80.

The obtained carboxylic acid (3.0 g) was reacted with 4 ml of thionyl chloride, and 3-benzyloxy-2,2-dimethylpropionyl chloride was obtained quantitatively as an oily material.

Infrared absorption spectra (CCl$_4$): ν: 1830, 1790, 1460, 1100, 915, 700 cm$^{-1}$

The obtained 3-benzyloxy-2,2-dimethylpropionyl chloride (3.4 g) was reacted with 1.1 g of H$_2$TamPP in the same manner as in Example 1, and the reaction mixture was purified by silica gel chromatography using a chloroform/ether (15/1) mixture as a solvent and then recrystallized from a mixed solvent of dichloromethane and methanol to give 1.92 g (yield 82%) of 5,10,15,20-tetra[α,α,α,α-o-(3-benzyloxy-2,2-dimethylpropanamido)phenyl]porphine. M.P. 170° to 172° C.

Infrared absorption spectra (KBr): ν: 3440, 3320, 2970, 2860, 1690, 1605, 1583, 1510, 1450, 1310, 1155, 1095, 1080, 970, 800, 755, 740, 700 cm$^{-1}$.

Proton NMR spectra (CDCl$_3$) $\delta_{ppm}$: −2.53 (2H, s, >NH in the porphine ring), 0.05 (24H, s, —C(CH$_3$)$_2$—CONH—), 2.72 (8H, s, PhCH$_2$OCH$_2$—), 3.29 (8H, s, PhCH$_2$OCH$_2$—), 6.46 to 6.56 (8H, m, —CH$_2$O—), 6.88 to 6.96 (12H, m, —CH$_2$O), 8.70 (8H, s, proton at the beta position of the porphine ring), 8.15 (4H, s, CO—NH—), 8.80 (4H, d, J = 7.3 Hz, CONH—), 7.33 to 7.90 (12H, m, CONH—).

Elemental analysis: C$_{92}$H$_{90}$N$_8$O$_8$; Calculated (%): C: 76.96, H: 6.32, N: 7.81; Found (%): C: 76.81, H: 6.41, N: 7.72.

EXAMPLE 10 (Formula (D), n=1)

In the same manner as in Example 2, 1.50 g of 5,10,15,20-tetra[α,α,α,α-o-(3-benzyloxyl-2,2-dimethylpropanamido)phenyl]porphine was reacted to remove its benzyl group, and the product was recrystallized from benzene to give 1.09 g (yield 96%) of 5,10,15,20-tetra[α,α,α,α-o-(3-hydroxy-2,2-dimethylpropanamido)phenyl]porphine. M.P. 294° to 297° C.

Infrared absorption spectra (KBr): ν: 3430 (broad), 3280 (broad), 1670, 1615, 1590, 1530, 1470, 1450, 1350, 1310, 1290, 1160, 1050, 970, 820, 810, 760 cm$^{-1}$.

Proton NMR spectra (CDCl$_3$): $\delta_{ppm}$: −2.89 (2H, brs, >NH in the porphine ring), −0.78 (2H, brs, hydrate H$_2$O), 0.49 (24H, s, —C(CH$_3$)$_2$CONH—), 1.02 (4H, brt, HOCH$_2$—), 2.22 (8H, d, J=4 Hz, HOCH$_2$C(CH$_3$)$_2$—), 7.35 (4H, s, —C(CH$_3$)$_2$—CONH—), 8.85 (8H, s, proton at the beta position of the porphine ring).

Elemental analysis: C$_{64}$H$_{66}$N$_8$O$_8$·H$_2$O; Calculated (%): C: 70.31, H: 6.27, N: 10.24; Found (%): C: 70.60, H: 6.34, N: 9.97.

EXAMPLE 11 (Formula (E), n=1)

In the same manner as in Example 3, 0.89 g of 5,10,15,20-tetra[α,α,α,α-o-(3-hydroxy-2,2-dimethylpropanamido)phenyl]porphine was reacted with ferrous bromide tetrahydrate, and the reaction mixture was purified with a mixed solvent of chloroform/methanol (50/1). Recrystallization from benzene/methanol gave 0.37 g (yield 38%) of bromo{5,10,15,20-tetra[α,α,α,α-o-(3-hydroxy-2,2-dimethylpropanamido)phenyl]porphinato}iron(III). M.P. higher than 300° C.

Infrared absorption spectra (KBr): ν: 3420 (broad), 3250 (broad), 1670, 1610, 1585, 1525, 1440, 1330, 1050, 1000, 800, 760, 720 cm$^{-1}$.

Elemental analysis: C$_{64}$H$_{64}$N$_8$O$_8$FeBr·H$_2$O; Calculated (%): C: 62.65, H: 5.42, N: 9.13; Found (%): C: 62.36, H: 5.46, N: 9.01.

EXAMPLE 12 (Formula (II), n=1)

In the same manner as in Example 4, 0.20 g of bromo{5,10,15,20-tetra[α,α,α,α-o-(3-hydroxy-2,2-dimethylpropanamido)phenyl]porphinato}iron(III) was reacted with 0.20 g of 2-chloro-2-oxo-1,3,2-dioxaphospholane and 0.20 ml of triethylamine. The reaction mixture was then reacted with 10 ml of trimethylamine, and the reaction mixture was purified with "Sephadex LH-60" using methanol as a solvent to give 0.15 g of iron(III)-5,10,15,20-tetra{α,α,α,α-o-[3-(2'-trimethylammonioethoxy)phosphinatoxy-2,2-dimethylpropanamido]phenyl}porphine complex as a black oily material.

Infrared absorption spectra (KBr): ν: 3400 (broad), 3040, 2970, 1650, 1480, 1260, 1090, 1060, 960, 760 cm$^{-1}$.

EXAMPLE 13 (Formula (F), n=10)

Pyridine, 1 ml, and then 1.09 g of 12-benzyloxy-2,2-dimethyldodecanoyl chloride were added dropwise to a solution of 2.1 g of H₂TamPP in 300 ml of dichloromethane, and the mixture was reacted for 3 hours at room temperature. After the reaction, 5 ml (an excessive amount) of pivaloyl chloride and 5 ml of pyridine were dropwise added, and the mixture was reacted for 2 hours. Saturated sodium hydrogen carbonate aqueous solution, 200 ml, was added to the resultant reaction mixture, and the separated organic layer was washed twice with 200 ml of a 4% sodium hydrogen carbonate aqueous solution and with 200 ml of water. After being dried over salt cake and concentrated under reduced pressure, the resultant residue was purified by silica gel column chromatography using a benzene/ether (7/1 v/v) mixture as a solvent, and then recrystallized from a mixed solvent of ether/methanol to give 1.26 g (yield 33%) of 5,10,15,20-[tri($\alpha,\alpha,\alpha$-o-pivalamidophenyl)-$\alpha$-o-(12-benzyloxy-2,2-dimethyldodecanamido)phenyl]porphine as red brown crystal. M.P. 87.5° to 89° C.

Field desorption mass spectrum: M⁺ 1242 ($C_{80}H_{90}N_8O_5=1242$).

Infrared absorption spectra (KBr): $\nu$: 3440, 3330, 2960, 2940, 2860, 1690, 1580, 1510, 1450, 1300, 1160, 970, 810, 760, 740 cm⁻¹.

Proton NMR spectra (CDCl₃): $\delta_{ppm}$: −2.60 (4H, s, >NH in the porphine ring), −0.21 (6H, s, —CH₂C(CH₃)₂CONH—), 0.05, 0.09 (27H, each s, (CH₃)₃C—CONH—), 3.46 (2H, t, J=6.4 Hz, PhCH₂OCH₂CH₂—), 4.50 (2H, s, PhCH₂O—), 7.85 (5H, s, phenyl proton of the benzyl group).

Elemental analysis: $C_{80}H_{90}N_8O_5$; Calculated (%): C: 77.26, H: 7.30, N: 9.01; Found (%): C: 76.89, H: 7.31, N: 8.88.

EXAMPLE 14 (Formula (G), n=10)

Anisole, 1 ml, and 2 g of anhydrous aluminum trichloride were added to a solution of the benzylether product (0.65 g) obtained in Example 13 in a mixed solvent of 15 ml of dichloromethane and 15 ml of nitromethane, and the mixture was reacted at room temperature for 3 hours. The reaction mixture was poured into 200 ml of iced water and extracted with 50 ml of chloroform. The separated chloroform layer was washed once with 100 ml of water and then twice with a 100 ml portion of a 4% sodium hydrogen carbonate aqueous solution. After being dried over salt cake, the layer was concentrated under reduced pressure to leave a residue which in turn was purified by silica gel column chromatography with a chloroform/ether (10/1) mixed solvent and then recrystallized from a benzene/n-hexane mixed solvent to give 0.43 g (yield 72%) of 5,10,15,20-[tri($\alpha,\alpha,\alpha$-o-pivalamidophenyl)-$\alpha$-o-(12-hydroxy-2,2-dimethyldodecanamido)phenyl]porphine as a red violet crystal. M.P. 220° to 221° C.

Infrared absorption spectra (KBr): $\nu$: 3650 to 3200 (broad), 3440, 3330, 2960, 2930, 2860, 1690, 1580, 1510, 1445, 1300, 1160, 970, 805, 750, 740 cm⁻¹.

Proton NMR spectra (CDCl₃): $\delta_{ppm}$: −2.60 (2H, s, >NH in the porphine ring), −0.19 (6H, s, —CH₂CH₂C(CH₃)₂—CONH—), 0.10, 0.06 (27H, each s, (CH₃)₃CCONH—), 3.79 (2H, t, J=6.5 Hz, HOCH₂CH₂—), 8.82 (8H, s, proton at the beta position of the porphine ring).

Elemental analysis: $C_{73}H_{84}N_8O_5$; Calculated (%): C: 76.01, H: 7.34, N: 9.72; Found (%): C: 76.17, H: 7.46, N: 9.43.

EXAMPLE 15 (Formula (H), n=10)

Ferrous bromide tetrahydrate, 0.6 g, was added to a solution of 0.575 g of the porphine obtained in Example 14 in 0.3 ml of pyridine and 40 ml of tetrahydrofuran under a nitrogen gas atmosphere, and the mixture was reacted for 4 hours under reflux conditions. The reaction mixture was concentrated under reduced pressure and the resultant residue was purified by alumina column chromatography with a chloroform/methanol (50/1) mixed solvent. 1 ml of 48% hydrobromic acid was added to the eluate, and the mixture was stirred. After being dried over salt cake, the mixture was concentrated under reduced pressure to leave a residue which in turn was recrystallized from a methanol/dichloromethane mixed solvent to produce 0.56 g (yield 87%) of bromo{5,10,15,20-[tri($\alpha,\alpha,\alpha$-o-pivalamidophenyl)-$\alpha$-o-(12-hydroxy-2,2-dimethyldodecanamido)phenyl]porphinato}-iron (III) as black violet crystal. M.P. 235° to 237° C.

Field desorption mass spectra: (M+1)⁺ 1287, (M+1)-Br⁺ 1207 ($C_{73}H_{82}N_8O_5$·FeBr=1286, Fe=57, and Br=79).

Infrared absorption spectra (KBr): $\nu$: 3440, 2970, 2940, 2860, 1690, 1585, 1510, 1445, 1300, 1260, 1000, 810, 760 cm⁻¹.

Elemental analysis: $C_{73}H_{82}N_8O_5FeBr$; Calculated (%): C: 68.11, H: 6.42, N: 8.70; Found (%): C: 67.84, H: 6.46, N: 8.58.

EXAMPLE 16 (Formula (III), n=10)

2-chloro-2-oxo-1,3,2-dioxaphospholane, 0.2 g, was added to a solution of 0.345 g of the compound obtained in Example 15 and 0.15 g of triethylamine in 20 ml of dichloromethane, and the mixture was reacted at room temperature for 12 hours. The reaction mixture was concentrated under reduced pressure, and the resultant residue was dissolved in 20 ml of acetonitrile. After the addition of 10 ml of trimethylamine, the solution was sealed in a container and reacted at 60° C. for 15 hours. The solvent was distilled off under reduced pressure and the resultant residue was dissolved in 100 ml of chloroform. After being washed with water, the separated chloroform layer was dried over salt cake and then concentrated under reduced pressure. The resultant residue was dissolved in methanol and the solution was purified by chromatography through a column packed with Toyopearl Gel HW-40s (Toyo Soda K.K.) using methanol as a solvent to give 0.086 g (yield 23%) of iron(III)-5,10,15,20-{tri($\alpha,\alpha,\alpha$-o-pivalamidophenyl)-$\alpha$-o-[12-(2'-trimethylammonioethoxy)phosphinato-2,2-dimethyldodecanamido]phenyl}porphine complex. M.P. 178° to 180° C.

Infrared absorption spectra (KBr): $\nu$: 3600–3200 (broad), 3440, 2960, 2940, 2860, 1690, 1582, 1510, 1445, 1300, 1070, 1000, 810, 760 cm⁻¹.

Elemental analysis: $C_{78}H_{94}N_9O_8P\cdot Fe\cdot 3H_2O$; Calculated (%): C: 65.67, H: 7.07, N: 8.83; Found (%): C: 65.34, H: 7.48, N: 8.80.

EXAMPLE 17 (Formula (A), n=10)

10-Benzyloxydecanyl bromide was prepared by reacting 100 g of 1,10-dibromodecane with an equimolar amount of sodium benzyloxide in tetrahydrofuran under reflux conditions, filtering the precipitated material, concentrating the filtrate and distilling the concentrated filtrate under reduced pressure. Yield 46 g. B.P. 185° to 189° C./3 mmHg.

According to the method reported by George R. Newkome et al.: Synthesis, 1975, 517, lithium dianion of 2-methylpropionic acid was generated from lithium diisopropylamide in tetrahydrofuran under a nitrogen atmosphere. After the dropwise addition thereto of 18 g of 10-benzyloxydecanyl bromide at −20° C., the mixture was reacted at 45° C. for 2 hours. The reaction mixture was then mixed with cold dilute hydrochloric acid and extracted with ether, and the separated ether layer was washed with dilute hydrochloric acid and then with water. The separated layer was then dried over salt cake and evaporated to dryness to leave a crude oily material which in turn was recrystallized from petroleum ether, producing 8.4 g (yield 46%) of 12-benzyloxy-2,2-dimethyldodecanoic acid as colorless crystal. M.P. 53° to 55° C.

Elemental analysis: $C_{21}H_{34}O_3$; Calculated (%): C: 75.40, H: 10.25; Found (%): C: 75.64, H: 10.09.

Proton NMR spectra ($CDCl_3$): $\delta_{ppm}$: 1.18 (6H, s, —C(CH_3)_2COOH), 1.26(16H, s, —OCH_2(CH_2)_8CH_2—), 3.46 (2H, t, PhCH_2OCH_2CH_2—), 4.51 (2H, s, PhCH_2O—), 7.33 (5H, s, phenyl proton).

1.2 ml of thionyl chloride was added to a solution of 3.34 g of the obtained carboxylic acid in 5 ml of anhydrous benzene, and the mixture was reacted at room temperature for 12 hours. The reaction mixture was concentrated under reduced pressure to give 3.53 g of 12-benzyloxy-2,2-dimethyldodecanoyl chloride as a colorless oily material.

Infrared absorption spectrum ($CCl_4$): $\nu$:

$1790^{-1}$ (—C(=O)—Cl).

Proton NMR spectra ($CDCl_3$): $\delta_{ppm}$: 1.28 (22H, s, —CH_3 and —CH_2—), 3.46 (2H, t, PhCH_2OCH_2CH_2—), 4.50 (2H, s, PhCH_2O—), 7.32 (5H, s, phenyl proton). (Oxygen Adsorption and Desorption Tests).

EXAMPLE 18

Figure 1:
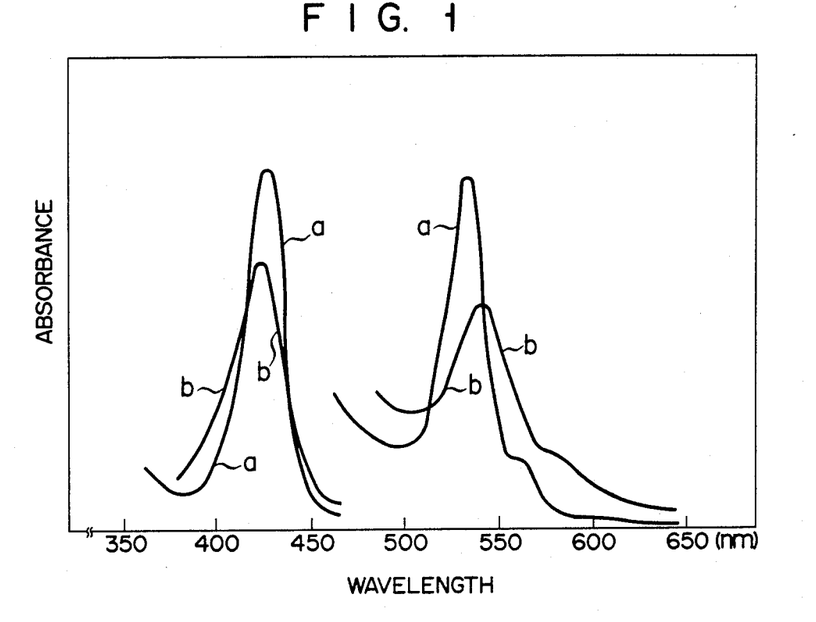
FIGS. 1 to 4 are graphs each showing oxygen adsorption and desorption capabilities of the iron-tetraphenylporphine complexes according to the present invention.

Iron(III)-5,10,15,20-tetra{α,α,60 ,α-o-[12-(2′-trimethylammonioethoxy)phosphinatoxy-2,2-dimethyldodecanamido]phenyl}porphine complex (0.586 mg) and N-phenethylimidazole included in α-cyclodextrin (a 1/1 molar clathrate/inclusion compound) (41 mg: 140-fold molar equivalent to the iron (III) complex) were dissolved in 9 ml of 0.1M phosphate buffer solution (pH 7.15). 1 mg of $NADP^+$, 8 mg of glucose-6-phosphate, 0.02 mg of ferredoxin, 0.1 mg of ferredoxin-NADP reductase and 0.05 mg of catalase as reducing enzymes were added to the solution. Nitrogen gas was then passed through this aqueous solution over a period of 20 minutes to remove oxygen. After the addition of 0.06 mg of glucose-6-phosphate dehydrogenase, the solution was allowed to stand at room temperature for 4 to 12 hours for reduction. By measuring the visible absorption spectrum, the formation of the hexacoordinated iron (II) porphyrin complex was confirmed by a spectrum as shown by the curves a in the attached drawing. Absorption maxima were at wavelengths of 427, 533 and 560 (shoulder) nm. Oxygen gas was passed through the aqueous solution, and then the spectra changed to those for the oxygen complex as shown by the curves b in the Figure. Absorption maxima were at wavelengths of 424 and 541 nm. Nitrogen gas was blown into this oxygen complex solution again so as to be under a nitrogen atmosphere and it was then confirmed that the spectra returned to those shown by the curved line a, showing that the oxygen was reversibly adsorbed/desorbed. It was also found that the half life of the oxygen complex solution was about 70 minutes, which was calculated by a variation over time in the visible absorption spectra of the oxygen complex solution.

The N-phenethylimidazole clathrate compound of α-cyclodextrin was prepared by the following procedures.

β-Bromoethylbenzene (10 g) and 10.6 g of imidazole were reacted at 200° C. for 5 hours, and the reaction mixture was extracted with 200 ml of chloroform. After being washed with a 10% sodium hydrogen carbonate aqueous solution and then with water, the resultant chloroform layer was separated and dried over salt cake. The solvent was then distilled off under reduced pressure and the residue was purified by distillation under reduced pressure to give 5.50 g (yield 45%) of N-phenethylimidazole as an oily material. B.P. 158° to 159° C./5 mmHg. A solution of 0.43 g of the obtained N-phenethylimidazole in 5 ml of ether was then added to a solution of 2.14 g of α-cyclodextrin in 50 ml of water, and the mixture was stirred at room temperature for 3 hours. The mixture was then lyophilized to give a colorless powder which in turn was washed twice with 50 ml of ether and dried under reduced pressure at 50° C. The product was dissolved in deuterium oxide, and it was confirmed from the proton integration ratio of the proton nuclear magnetic resonance spectra that the product was a clathrate compound of α-cyclodextrin and N-phenethylimidazole in a molar ratio of 1 to 1.

EXAMPLE 19

Albumin was added to the solution used in Example 18 so as to amount for 5% (w/v) in concentration and, after being likewise reduced, the reversible adsorption/desorption of oxygen was confirmed by the visible absorption spectra. The half life of the resultant oxygen complex was stable for longer than 180 minutes. There was also found to be no difference between naturally occurring albumins originating from human serum, bovine serum, sheep serum, rabbit serum, mouse serum and chicken serum.

EXAMPLE 20

A solution of 2.7 mg of iron(III)-5,10,15,20-tetra{α,α,α,α-o-[20-(2′-trimethylammonioethoxy)phosphinatoxy-2,2-dimethyleicosanamido]phenyl}porphine complex, 2.2 mg of N-laurylimidazole and 35 mg of egg yolk phosphatidyl choline in methanol was formed into a thin layer under reduced pressure on the wall of a round-bottomed flask and dried. 12 ml of physiological saline was added to this, and the container content was stirred to produce an emulsion which in turn was ultrasonicated to make the solution almost transparent. Nitrogen gas was blown into this solution for 20 minutes to remove oxygen therefrom, and the enzymes used in Example 18 were added. The mixture was left to stand at room temperature for 12 hours to permit the reduction of the product to thereby give an iron(II)-porphine complex solution. The adsorption and desorption of oxygen was observed in the same manner as in Example 18, and the half life of the oxygen complex was seen from a variation over time in visible absorption spectra to be stable for longer than 5 hours. The reduction type had absorption maxima at wavelengths of 533 and 562 nm (shoulder), and the oxygen complex at 540 nm.

EXAMPLE 21

The procedures used in Example 20 were followed with the exception that 35 mg of dimyristoylphosphatidyl choline was employed in place of egg yolk phosphatidyl choline. Tests conducted in the same manner as before showed identical results for the absorption maxima locations and the half life of the oxygen complex.

EXAMPLE 22

A solution of 1.24 mg of the iron(III)-porphine complex synthesized in Example 16, 1.06 mg of N-laurylimidazole (5-fold molar equivalent to the iron(III) complex) and 66 mg of egg yolk phosphatidyl choline (about 50-fold equivalent to the iron(III) complex) in a chloroform/methanol solution was formed into a thin layer under reduced pressure on the wall of a round-bottomed flask and dried. The addition of 10 ml of a 0.1M phosphate buffer solution and stirring gave an emulsion which in turn was ultrasonicated for 30 minutes under a nitrogen atmosphere to give an aqueous solution in which liposome containing the iron(III) complex was homogeneously dispersed. Nitrogen gas was blown into this solution for 20 minutes to remove oxygen therefrom and, as enzymes, 1 mg of NADP+, 10 mg of glucose-6-phosphate, 0.02 mg of ferredoxin, 0.1 mg of ferredoxin-NADP+ reductase, 0.05 mg of catalase and 0.08 mg of glucose-6-phosphate dehydrogenase were added. The mixture was allowed to stand at room temperature for 6 hours for reduction to give an iron(II)-porphine complex liposome solution, which was found to be of the reduction type having absorption spectrum maxima at wavelengths of 427, 533 and 560 (shoulder) nm as a result of visible absorption spectrum measurement. Oxygen gas was then blown into this solution for a period of 30 seconds. It was confirmed that the spectra changed immediately thereafter to show absorption spectra maxima at 424 and 538 nm, whereat the oxygen complex absorption spectrum maxima were located. Nitrogen gas was blown again into this solution for 2 minutes so as to recover a nitrogen atmosphere. It was found that the spectra changed back to the reduced type showing absorption spectrum maxima at 427, 533 and 560 (shoulder) nm. This means that the adsorption and desorption of oxygen occured reversibly. The half life of the oxygen complex was found to be as long as about 2 hours as a result of a variation over time in visible absorption spectra.

EXAMPLE 23

Figure 2:
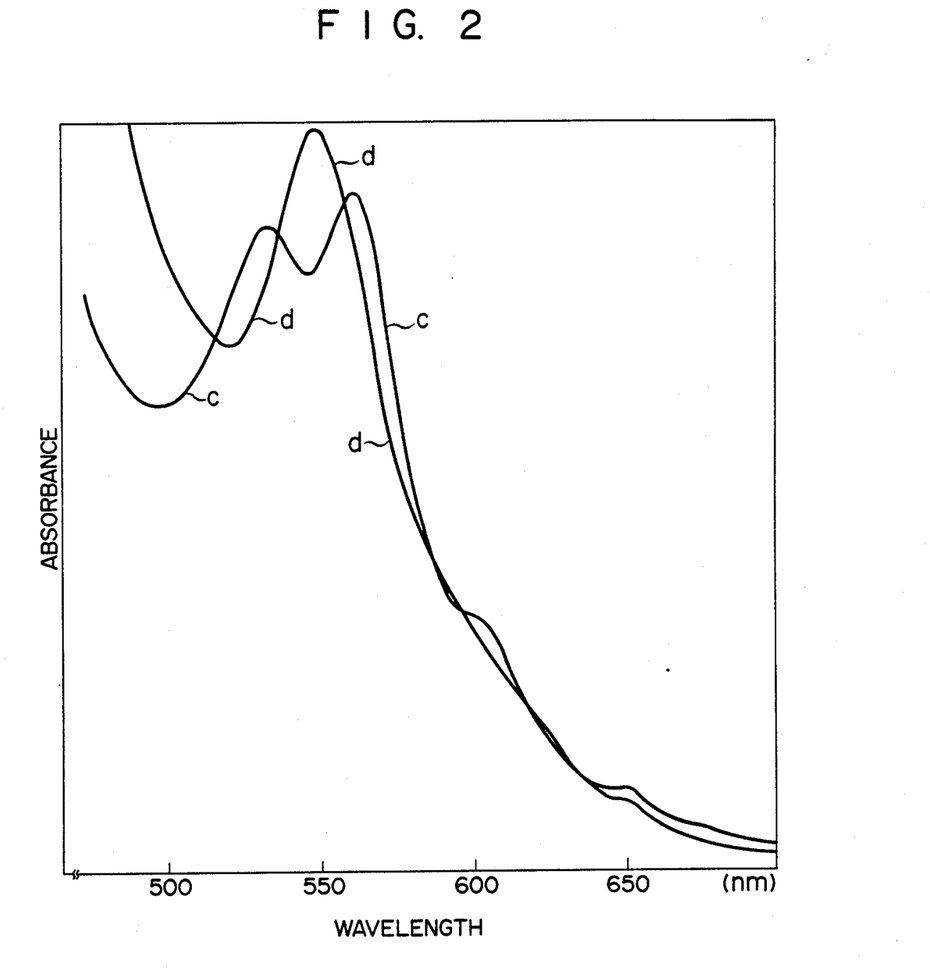

Palladium black, 5 mg, was added to a solution of 1.72 mg of iron(III)-5,10,15,20-tetra{$\alpha,\alpha,\alpha,\alpha$-o-[20-(2'-trimethylammonioethoxy)phosphinatoxy-2,2-dimethyleicosanamido[phenyl]}porphine complex, 7.6 mg of 1-lauryl-2-methylimidazole (50-fold molar equivalent to the complex) and 0.1 g of "Triton X-100" (Rohm and Haas) as a synthetic surface active agent in 10 ml of methanol, and hydrogen gas was blown into the mixture for 40 minutes for reduction. The palladium black was filtered off under a hydrogen gas atmosphere and the filtrate was treated by means of a vacuum pump to distill off the solvent under reduced pressure. 10 ml of 0.05M phosphate buffer solution (pH 7.0) was added to the residue under a nitrogen gas atmosphere, which had been lyophilized and dehydrated, and the mixture was stirred to give a homogeneous aqueous solution (1.0% (w/v) "Triton X-100" aqueous solution) containing the iron(II)-porphine complex. The measurement of visible absorption spectra confirmed a spectrum for the penta-coordination of the central iron of the reduction type showing a conversion from trivalency to divalency. It was also confirmed that absorption maxima were given at wavelengths of 532 and 561 nm. The passing of oxygen gas through this solution resulted in an immediate change in spectra as shown by the curve d in FIG. 2, and was found to give an oxygen complex having an absorption spectrum maxima at a wavelength of 547 nm. By passing nitrogen gas into the oxygen complex solution so as to become nitrogen atmosphere, it was found that the spectra returned to those as shown by the curve c in FIG. 2, whereby the reversible adsorption and desorption of oxygen was confirmed. Although the obtained oxygen complex solution was oxidized slowly over time, the half life of this solution was found to be about 5 hours as a result of visible absorption spectrum measurement.

EXAMPLE 24

By measuring the oxygen binding curve, it was clarified that the complex according to the present invention either bound or released the oxygen according to a variation in the oxygen partial pressures.

A solution of 9.56 mg ($3.37 \times 10^{-3}$ mmoles) of iron-(III)-5,10,15,20-tetra{$\alpha,\alpha,\alpha,\alpha$-o-[20-(2'-trimethylammonioethoxy)phosphinatoxy-2,2-dimethyleicosanamido]phenyl}porphine complex, 7.95 mg ($3.37 \times 10^{-2}$ mmoles) of N-laurylimidazole and 246 mg ($3.37 \times 10^{-1}$ mmoles) of egg yolk phosphatidyl choline in methanol was formed into a thin layer under reduced pressure on the wall of a flask and dried. 80 ml of a 0.05M phosphate buffer solution (pH 7.0) was added to this, and the flask content was stirred to form an emulsion which in turn was ultrasonicated at 30 W for 30 minutes until the emulsion became almost transparent. Nitrogen gas was blown into this solution for 30 minutes to remove oxygen therefrom, and 11.8 mg ($6.76 \times 10^{-2}$ mmoles) of ascorbic acid was added. The mixture was then incubated at 37° C. for 2 hours for reduction to give an iron(II)-porphine complex solution.

Figure 3:
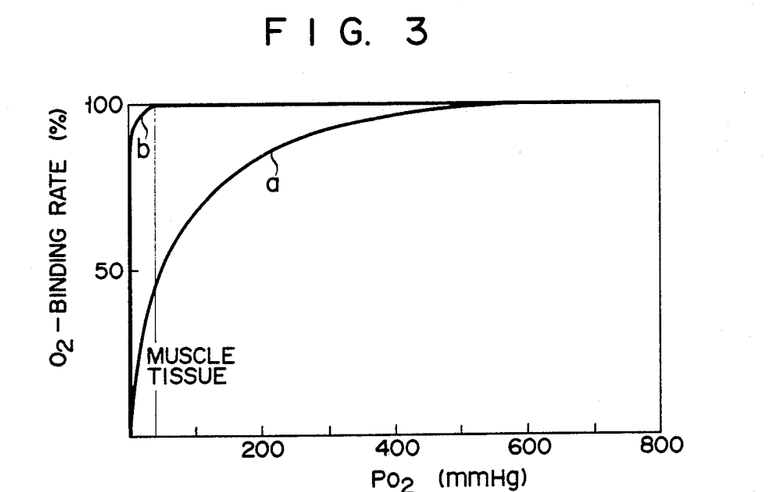

While oxygen was blown piecemeal into the solution, a variation in absorbency at $\lambda_{max}$ 533 nm based on the deoxy complex was measured by means of a UV-Vis Spectrophotometer (Shimadzu UV-300, Shimadzu Seisakusho, Kyoto, Japan). The absorbency gradually reduced with the formation of the oxygen complex. At the same time, the concentration of the oxygen dissolved in the solution was also measured by means of a dissolved oxygen measuring device (Shimadzu DOA-1) and the oxygen binding-dissociation curve as shown by the curve a in FIG. 3 was obtained. The curve b in FIG. 3 shows an oxygen binding-dissociation curve obtained by measuring myoglobin in muscle tissues in the same manner as above.

From this figure, it is to be understood that the iron-(II)-porphine complex solution according to the present invention releases, for example, about 55% of the oxygen bound under oxygen partial pressure conditions at about 40 mmHg at which tissues of the peripheral blood vessel are under oxygen partial pressure conditions. It is thus apparent that all the released oxygen are bound and received under the same oxygen partial pressure conditions by mioglobin that is present in peripheral muscle tissues and functions as storage of oxygen. This indicates that the complex according to the present invention is capable of transferring oxygen within a living body.

EXAMPLE 25

In order to study the incorporation of the compound of the invention in a loposome, the following experiment was carried out.

Figure 4:
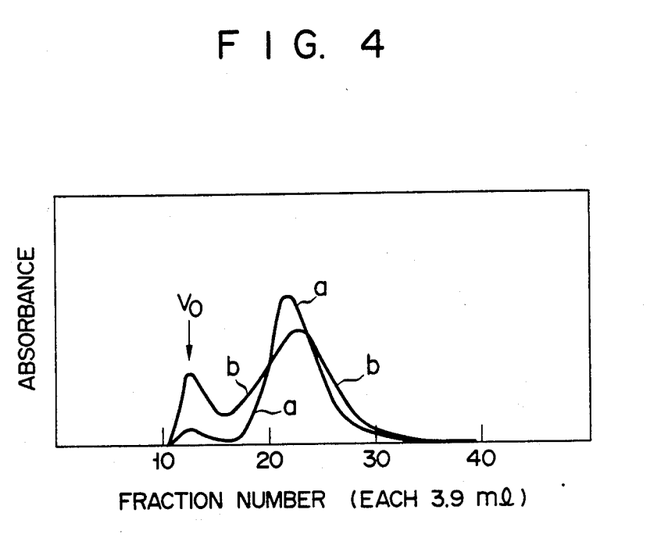

A solution of 9.56 mg ($3.37 \times 10^{-3}$ mmoles) of iron-(III)-5,10,15,20-tetra{α,α,α,α-o-[20-(2'-trimethylammonioethoxy)phosphinatoxy-2,2-dimethyleicosanamido]phenyl}porphine complex, (II) (n=18), 7.95 mg ($3.37 \times 10^{-2}$ mmoles) of N-laurylimidazole and 246 mg ($3.37 \times 10^{-1}$ mmoles) of egg yolk phosphatidyl choline in methanol was formed into a thin layer under reduced pressure on the wall of a flask and dried. 80 ml of a 0.05M phosphate buffer solution (pH 7.0) was added to this, and the flask content was stirred to form an emulsion which in turn was ultrasonicated at 30 W for 30 minutes until the emulsion became almost transparent. The same procedures were followed with the exception that the iron(III)-5,10,15,20-tetra{α,α,α,α-o-[12-(2'-trilmethylammonioethoxy)phosphinatoxy-2,2-dimethyleicosanamido]-phenyl}porphine complex, (II) (n=10), was employed in place of the iron-porphine complex described above. The resultant solution were examined by gel permeation on Sepharose 4B (2×50 cm) with the same buffer, and the elution curves are shown in FIG. 4. The void volume ($V_0$) was determined by blue dextran-2000. The curve a shows the elution curve of compound (II) (n=18) and the curve b shows the elution curve of compound (II) (n=10) detected with 415 nm. The elution pattern indicates that the iron(III)-porphine complexes are embedded in the liposome of egg yolk phosphatidyl choline.

What is claimed is:

1. An iron-5,10,15,20-tetra(α,α,α,α-o-substituted phenyl)porphine complex having a structure represented by the general formula:

where each of R is identical and stands for

(a pivalamido group) or the group n is an integer from 1 to 20, and the central iron atom is divalent or trivalent.

2. A complex according to claim 1, having a general formula:

3. A complex according to claim 1, having a general formula:

4. An oxygen adsorbing and desorbing agent comprising:

an iron-5,10,15,20-tetra($\alpha,\alpha,\alpha,\alpha$-o-substituted phenyl)porphine complex having a structure represented by the general formula:

wherein each of R is identical and stands for

(a pivalamido group) or the group n is an integer from 1 to 20, and the central iron atom is divalent; and a basic ligand coordinated at the central iron atom of the complex.

5. An oxygen sorbent according to claim 4, wherein the basic ligand has a formula:

wherein $R_1$, $R_2$ and $R_3$ are independently each hydrogen, methyl or ethyl; and $R_4$ is hydrogen, a $C_1$–$C_{20}$ alkyl group, phenyl group, benzyl group, phenethyl group or trityl group.

* * * * *